US007235350B2

United States Patent
Schulman et al.

(10) Patent No.: US 7,235,350 B2
(45) Date of Patent: Jun. 26, 2007

(54) ALUMINA INSULATION FOR COATING IMPLANTABLE COMPONENTS AND OTHER MICROMINIATURE DEVICES

(75) Inventors: Joseph H. Schulman, Santa Clarita, CA (US); Joseph Y. Lucisano, San Diego, CA (US); Rajiv Shah, Rancho Palos Verdes, CA (US); Charles L. Byers, Canyon Country, CA (US); Shaun M. Pendo, Santa Maria, CA (US)

(73) Assignee: Alfred E. Mann Foundation, Sylmar, CA (US)

( * ) Notice: Subject to any disclaimer, the term of this patent is extended or adjusted under 35 U.S.C. 154(b) by 0 days.

(21) Appl. No.: 10/969,758

(22) Filed: Oct. 20, 2004

(65) Prior Publication Data

US 2005/0106366 A1    May 19, 2005

Related U.S. Application Data

(60) Division of application No. 10/251,633, filed on Sep. 20, 2002, now Pat. No. 6,844,023, which is a continuation of application No. 09/393,438, filed on Sep. 9, 1999, now Pat. No. 6,472,122, and a division of application No. 08/994,515, filed on Dec. 19, 1997, now Pat. No. 6,043,437.

(60) Provisional application No. 60/033,637, filed on Dec. 20, 1996.

(51) Int. Cl.
*B32B 3/00* (2006.01)
*B32B 18/00* (2006.01)

(52) U.S. Cl. ............... 430/315; 204/192.11; 428/209; 428/210; 428/469; 428/701

(58) Field of Classification Search .............. 430/311, 430/30; 428/209, 210, 469, 701; 204/192.11, 204/192.15
See application file for complete search history.

(56) References Cited

U.S. PATENT DOCUMENTS

| 4,777,494 A | * | 10/1988 | Shibata et al. ............... 347/64 |
| 5,265,143 A | * | 11/1993 | Early et al. .................. 378/84 |
| 5,665,657 A | * | 9/1997 | Lee ............................ 438/624 |
| 5,750,926 A | * | 5/1998 | Schulman et al. ......... 174/52.3 |

FOREIGN PATENT DOCUMENTS

JP    63-276030    * 11/1988

* cited by examiner

*Primary Examiner*—John A. McPherson
*Assistant Examiner*—Daborah Chacko-Davis
(74) *Attorney, Agent, or Firm*—Foley & Lardner LLP

(57) ABSTRACT

A protective, biocompatible coating or encapsulation material protects and insulates a component or device intended to be implanted in living tissue. The coating or encapsulation material comprises a thin layer or layers of alumina, zirconia or other ceramic, less than 25 microns thick, e.g., 5-10 microns thick. The alumina layer(s) may be applied at a relatively low temperature. Once applied, the layer provides excellent hermeticity, and prevents electrical leakage. Even though very thin, the alumina layer retains excellent insulating characteristics. In one embodiment, an alumina layer less than about 6 microns thick provides an insulative coating that exhibits less than 10 pA of leakage current over an area 75 mils by 25 mils area while soaking in a saline solution at temperatures up to 80° C. over a three month period.

10 Claims, 5 Drawing Sheets

ALUMINA INSULATION FOR COATING IMPLANTABLE COMPONENTS AND OTHER MICROMINIATURE DEVICES

This application is a divisional of application Ser. No. 10/251,633 filed Sep. 20, 2002 (now U.S. Pat. No. 6,844,023 issued Jan. 18, 2005), which is a continuation of application Ser. No. 09/393,438, filed Sep. 9, 1999 (now U.S. Pat. No. 6,472,122 issued Oct. 29, 2002). Application Ser. No. 09/393,438 is a divisional of application Ser. No. 08/994,515 filed Dec. 19, 1997 (now U.S. Pat. No. 6,043,437 issued Mar. 28, 2000) which in turn claims the benefit of U.S. provisional Application Ser. No. 60/033,637 filed Dec. 20, 1996, the contents of each are incorporated by reference herein.

BACKGROUND OF THE INVENTION

The present invention relates to very thin layers of electrical insulation that may be used to coat and protect microminiature components and devices that are intended to be implanted in living tissue and/or to maintain electrical leakage of such components/devices within acceptable limits, e.g., less than 1 $\mu A/cm^2$ when the components and/or devices are submerged in water or salt water. More particularly, the invention relates to the use of alumina or aluminum oxide as a safe, biocompatible, coating material that provides a reliable, protective and insulative layer or coating for components, or devices comprised of components, wherein the insulating layers can be made extremely thin, on the order of microns, yet wherein the electrical leakage through the thin insulative layer (when the coated component or device is implanted or otherwise immersed in a saline solution or in distilled water) is less than about 1 $\mu A/cm^2$ (or less than about 12.1 nA for an area of 0.075 inches×0.025 inches, corresponding to an area of 0.1905 cm by 0.0635 cm).

The use of alumina as a thick insulator for use with implantable devices has previously been disclosed, for example, in U.S. Pat. Nos. 4,940,858 and 4,678,868 assigned to Medtronic, Inc. In these applications, however, the alumina insulator is very thick and is used only as part of the feedthrough for the implantable device and is often carried by a metal ferrule. Such use of alumina (or other ceramic) as an insulator requires a relatively thick layer. Many materials work well as an insulator when put down in a thick layer, e.g., in a layer thicker than 25 microns (where 1 micron=1×$10^{-6}$ meter). But all such materials, except as discussed herein, typically leak at a rate greater than about 1 $\mu A/cm^2$. Applicants invention, as set forth below, uses a nonconductive ceramic, such as alumina, in very thin layers, e.g., less than about 25 microns.

It is also known to use the ceramic alumina as a case material for an implanted device as disclosed in U.S. Pat. No. 4,991,582, incorporated herein by reference. Again, however, the alumina, while comprising a material that is biocompatible (and is thus not harmful to, and is not harmed by, living tissue and fluids wherein it is implanted), is relatively thick, e.g., greater than 25 microns.

A problem with the related art is that the thickness of the insulation needed for implantable devices is typically on the order of about several millimeters thick. None of the related art, to applicant's knowledge, has heretofore achieved an insulating layer with very small dimensions and free of micro-holes. The presence of a micro-hole, or "pin-hole", destroys the insulating properties which may lead to eventual failure of the implantable device.

Further, some components or devices which need to be implanted in living tissue, such as magnets, are susceptible to extremely high temperatures, i.e., extremely high temperatures may damage or destroy such components. When such components or devices must be implanted, it is important therefore that whatever coating or encapsulating material is used to coat them be one that can be applied without subjecting the component or device to extremely high temperatures. That is, the coating or application process must not subject such components to extremely high temperatures.

It is seen, therefore, that what is needed is a way to utilize a very thin layer of a suitable insulating material, such as alumina (aluminum oxide), zirconia (zirconium oxide), or alloys of alumina and/or zirconia, at relatively low temperatures, as a coating to cover, insulate and/or encapsulate any type of component or device that must be implanted, thereby effectively rendering such coated component or device biocompatible and safe for implantation. In particular, it is seen that what is needed is a very thin insulative coating that can be applied at relatively low temperatures for the purpose of insulating electrical connections on implantable devices and other microminiature devices, or for coating non-biocompatible components (thereby making the coated component biocompatible) wherein the coating can be as thin as about $\frac{1}{1000}$ of an inch or less yet still maintain the electrical leakage through the insulator at or below acceptable levels.

The present invention addresses the above and other needs.

SUMMARY OF THE INVENTION

The present invention provides a protective, biocompatible coating or encapsulation material that may be applied to a component or device intended to be implanted in living tissue. The coating or encapsulation material comprises a thin layer or layers of alumina, zirconia, and/or alloys of alumina and/or zirconia. Advantageously, a thin alumina or zirconia layer applied in accordance with the present invention may be applied at relatively low temperature. Once applied, the coating provides excellent hermeticity, and prevents electrical leakage, while retaining a microminiature size. The layer of alumina or zirconia insulation can be made as thin as about $\frac{1}{1000}$ of an inch (Note: $\frac{1}{1000}$ inch=0.001 inch=1 mil=25.4 microns) or less while still retaining excellent insulating characteristics. For example, in accordance with one aspect of the present invention, an alumina coating having a thickness that is less than about 5-10 microns provides an insulative coating that exhibits less than about 12 nA of leakage current over an area 75 mils by 25 mils while soaking in a saline solution at temperatures up to 80° C. over a three month period.

Advantageously, the invention may be used to encapsulate or coat (and thereby insulate) passive electrical and/or magnetic components, such as resistors, capacitors, inductors, wire, conductive strips, magnets, diodes, etc., and/or active electrical components, such as transistors, integrated circuits, etc., and/or assemblies or combinations of such passive and/or active components. Because the coating layer can be made extremely thin, yet still provide the needed insulative properties required for an implanted component or device, the overall size of such components or devices does not increase significantly from the normal size (non-implanted size) of such components or devices. For many applications, e.g., as taught in U.S. Pat. No. 5,193,539, incorporated herein by reference, a complete implanted device, comprised of many different components, may be coated and maintained at a microminiature size. For other applications, e.g., the implantation of one or more permanent magnets, such magnets may be coated with the alumina or zirconia coating, thereby effectively hermetically sealing the magnets in an alumina or zirconium encapsulation that renders the magnets suitable for direct implantation in living body tissue at a desired location.

It is an object of the invention to provide a biocompatible, thin, insulative coating that is easy to apply to a wide variety of different shapes and sizes of components and devices, and that once applied provides excellent insulative properties for the covered component or device over a long period of time, thereby allowing the covered component or device to be safely implanted in living tissue for long periods of time.

It is a further object of the invention, in accordance with one aspect thereof, to provide a biocompatible, insulative coating that may be applied to implantable components or devices of various shapes and sizes, and wherein the coating is: (1) less than about 10 microns thick; (2) submersible for long periods of time in water or saline solution or any other conductive fluids; (3) made from alumina, zirconia or alloys of alumina and/or zirconia, or other substances having properties the same as or similar to alumina, zirconia and/or alloys of alumina and/or zirconia; (4) amenable to being applied using a batch process, e.g., a process wherein 1000 or more devices or components may be coated at the same time using the same process, such as an evaporative coating, vapor deposition, or ion-beam deposition (IBD) process; and/or (5) extremely strong in the lateral direction.

BRIEF DESCRIPTION OF THE DRAWINGS

The above and other aspects, features and advantages of the present invention will be more apparent from the following more particular description thereof, presented in conjunction with the following drawings, wherein.

DETAILED DESCRIPTION OF THE INVENTION

The following description is of the best mode presently contemplated for carrying out the invention. This description is not to be taken in a limiting sense, but is made merely for the purpose of describing the general principles of the invention.

In the description of the invention herein, reference is frequently made to a "layer of alumina" or to an "alumina insulation layer" as the preferred material for the coating or layer that comprises the invention. Alumina, as is known in the art, comprises a shorthand notation for aluminum oxide, $Al_2O_3$. It is to be understood that all such references to an insulating layer or coating made from "alumina" also apply to an insulating layer made from other suitable substances, such as magnesium oxide, zirconium oxide (zirconia), alloys of alumina and/or zirconia, and the like. In general, such oxides may be referred to as ceramics.

An alumina insulation layer or coating for microminiature or other devices is applied by depositing one or successive layers of alumina to electrical connections and/or other electronic circuitry or components. In some cases, the component or object to be coated may comprise an IC chip by itself.

Each insulating layer applied is preferably made by depositing aluminum oxide ("alumina"), or other suitable insulating material, so as to coat the desired surface of the component or device.

Figure 1A:
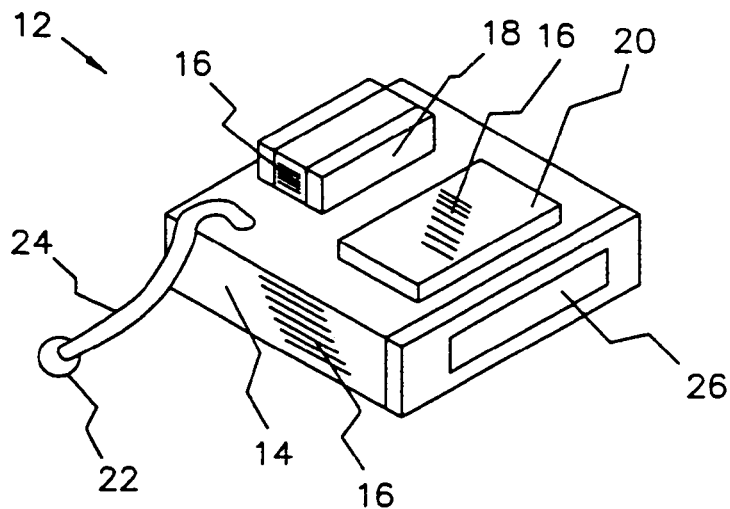
FIG. 1A illustrates an electronic device that has been coated with a thin insulative layer in accordance with the present invention.

A common application for the alumina insulating coating of the present invention is to insulate or encapsulate the entire surface of a hybrid integrated circuit 12 formed on a ceramic substrate 14, once the hybrid integrated circuit 12 has been formed, with an insulative layer 16, as illustrated in FIG. 1A. In FIG. 1A, by way of example, the substrate 14 may have a capacitor 18 and an integrated circuit chip 20 mounted thereon, both of which are also coated with the insulative layer 16. Depending upon the function of the hybrid circuit 12, an electrode 22 may also be connected thereto via a coated wire 24. Also, to provide a return path from the electrode 22, a portion of the layer 16 that covers one end of the substrate 14 may be removed, thereby exposing a return electrode 26.

For other applications, the alumina insulating coating is applied to insulate or encapsulate just the integrated circuit (IC) chip 20 by itself. Any electrical connections that may need to be made to the IC chip, e.g., via an insulated wire, may be made prior to application of the insulating coating. In such instance, the IC 20 once coated could then be implanted directly into living tissue yet still perform its intended function.

Figure 1B:
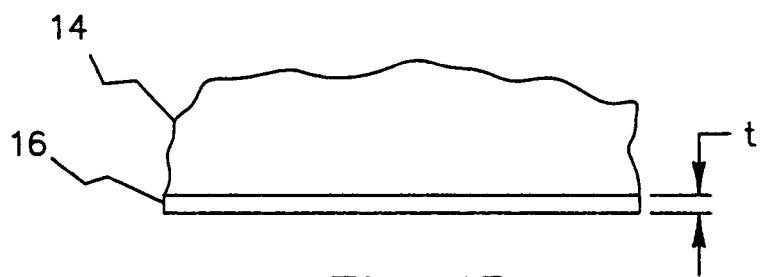
FIG. 1B shows an enlarged side view of a portion of the substrate of FIG. 1A so as to depict the alumina layer thereon.

The insulative layer 16 is very thin, having a thickness "t" on the order of 5-25 microns. Thus, the layer 16 is not readily visible in FIG. 1A, but is represented in the enlarged and magnified side view of FIG. 1B.

Figure 2:
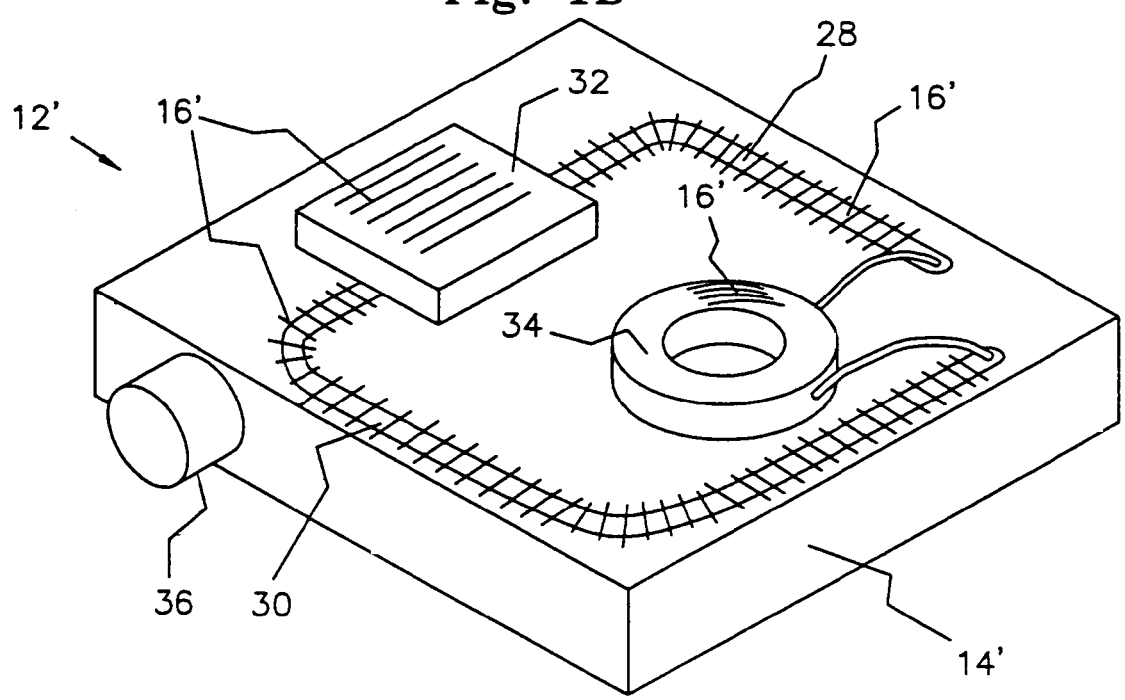
FIG. 2 shows a component coated with a thin insulative layer in accordance with the invention, thereby rendering such component (which without the coating may be non-bio-compatible and non-implantable) both biocompatible and implantable.

Alternatively, an insulating coating 16' may be used to insulate selected metal traces 28 and 30, or components 32 and 34, mounted on or to a ceramic substrate 14' of a hybrid integrated circuit 12', while other components, such as electrode 36, or some portions of the surface of the substrate 14', are not coated or encapsulated, as illustrated in FIG. 2A. In FIG. 2A, those components or surface areas not to be coated with the layer 16' may be masked using conventional techniques at the time the coating 16' is applied.

Figure 3:
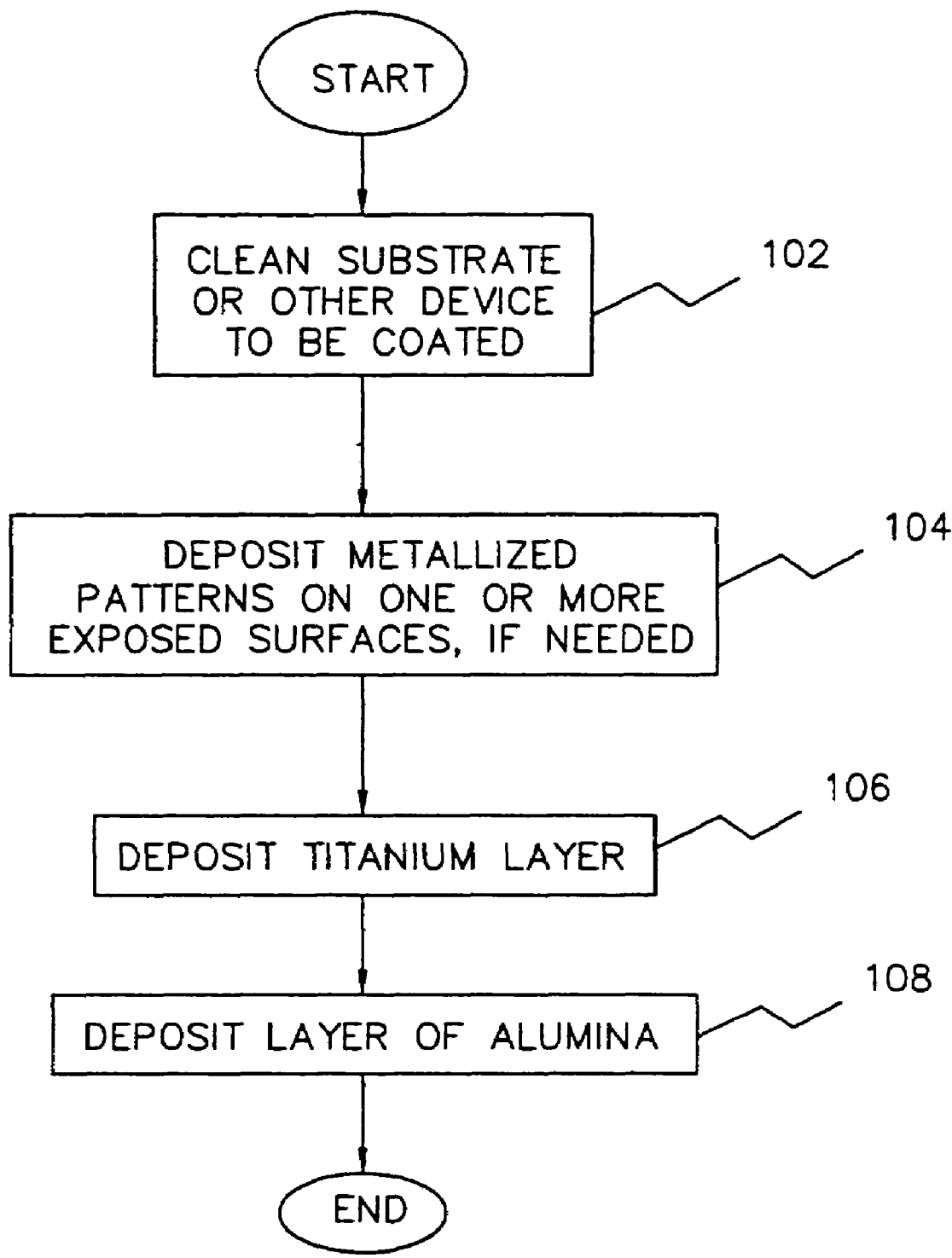
FIG. 3 is a flow chart that depicts, in general steps, the method of applying a coating in accordance with the invention.

In general terms, and for applications where a hybrid circuit, an IC chip, or other device is to be coated with alumina in accordance with the encapsulation/coating process of the present invention, the steps followed by the invention are illustrated in FIG. 3 and may be summarized as:

(1) Atomically cleaning an insulating substrate or IC chip (if necessary) with a plasma cleaning, or equivalent, process (block 102 of FIG. 3). Note: if an IC chip is being coated by itself, and if the IC chip has not yet left its clean fabrication environment, this step may not be needed. The insulating substrate, when used, may be made from, or already coated with, successive layers of alumina or other suitable insulating material, such as magnesium oxide or zirconia.

(2) Depositing metallized patterns of a suitable conductive material on one or more of the exposed surfaces of the substrate (block 104). The metallized patterns are preferably deposited or etched on the substrate using conventional thin film deposition, painting or metalized etching techniques, as are common in the printed circuit board and integrated circuit fabrication arts. These patterns are used to make desired electrical connections between components of the circuit.

(3) Depositing a layer of titanium on the metallized portions of alumina substrate (block 106). Typically, such layer of titanium will be about 300 Å thick.

(4) Depositing additional layers of alumina, using an ion-enhanced evaporative sputtering technique, or ion beam deposition (IBD) technique, over the entire surface of the substrate including the metallized traces. Using an IBD technique, for example, one application of alumina may lay down a layer of alumina that is only 1-2 microns thick. Through application of several such layers, an alumina coating may thus be formed of sufficient thickness to provide the desired insulative (leakage current) and encapsulation (hermeticity) properties. Advantageously, the deposited alumina coating (comprising a plurality of deposited layers) need only be 5-10 microns thick.

Various techniques may be used to apply the alumina insulation over the device or component that is to be insulated. A preferred technique, for example, is to use an ion beam deposition (IBD) technique. IBD techniques are known in the art, as taught, e.g. in U.S. Pat. No. 4,474,827 or U.S. Pat. No. 5,508,368, incorporated herein by reference.

Figure 4:
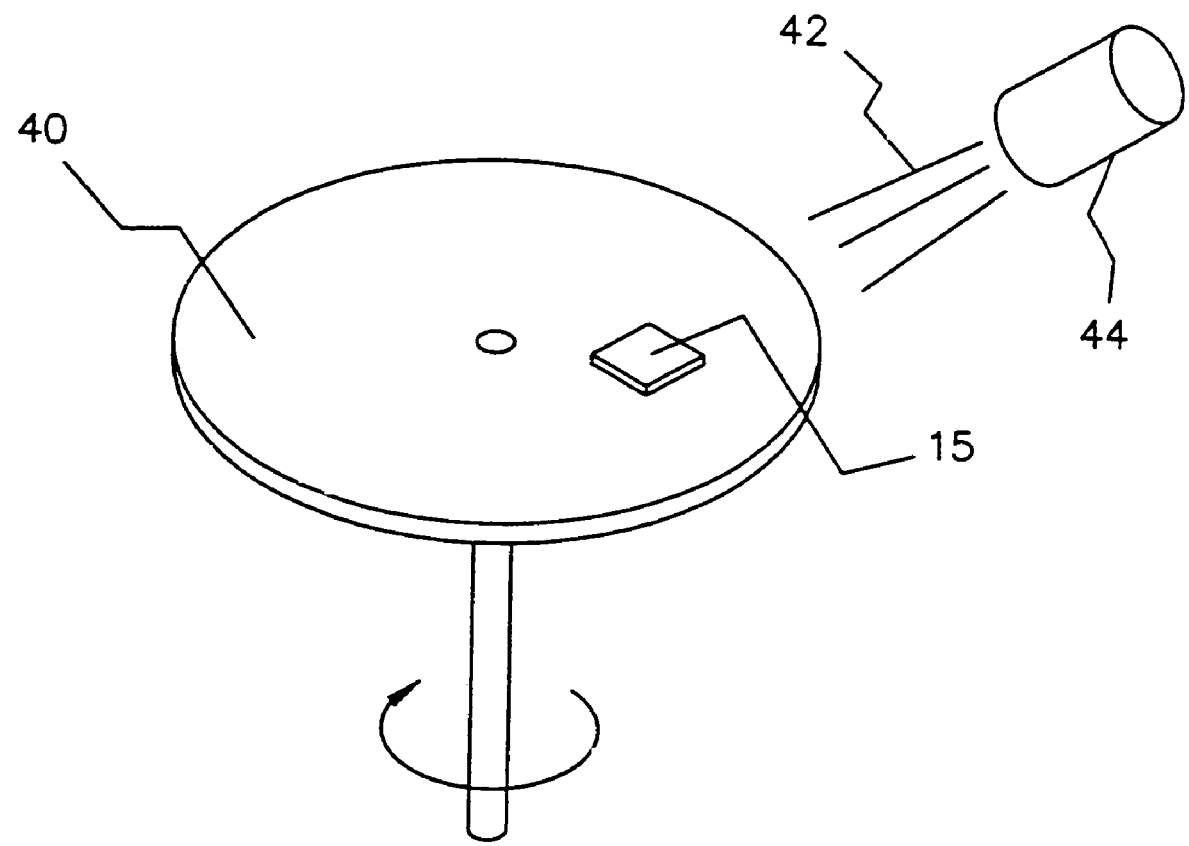
FIG. 4 schematically depicts one method that may be used to coat five of six sides of an object with an insulative coating in accordance with the present invention.

Using such IBD techniques, or similar techniques, the desired alumina layer may be deposited on all sides of an object 15 as illustrated in FIG. 4. As seen in FIG. 4, the object 15 is placed on a suitable working surface 40 that is rotatable at a controlled speed. The working surface 40, with the object 15 thereon, is rotated while a beam 42 of ions exposes the rotating surface. Assuming the object 15 has six sides, five of the six sides are exposed to the beam 42 as it rotates, thereby facilitating application of the desired layer of alumina onto the five exposed sides of the object. After sufficient exposure, the object is turned over, thereby exposing the previously unexposed side of the object to the beam, and the process is repeated. In this manner, four of the sides of the object 15 may be double exposed, but such double exposure is not harmful. Rather, the double exposure simply results in a thicker coating of alumina on the double-exposed sides.

Other techniques, as are known in the art, may also be used to apply the alumina coating to the object.

Figure 5:
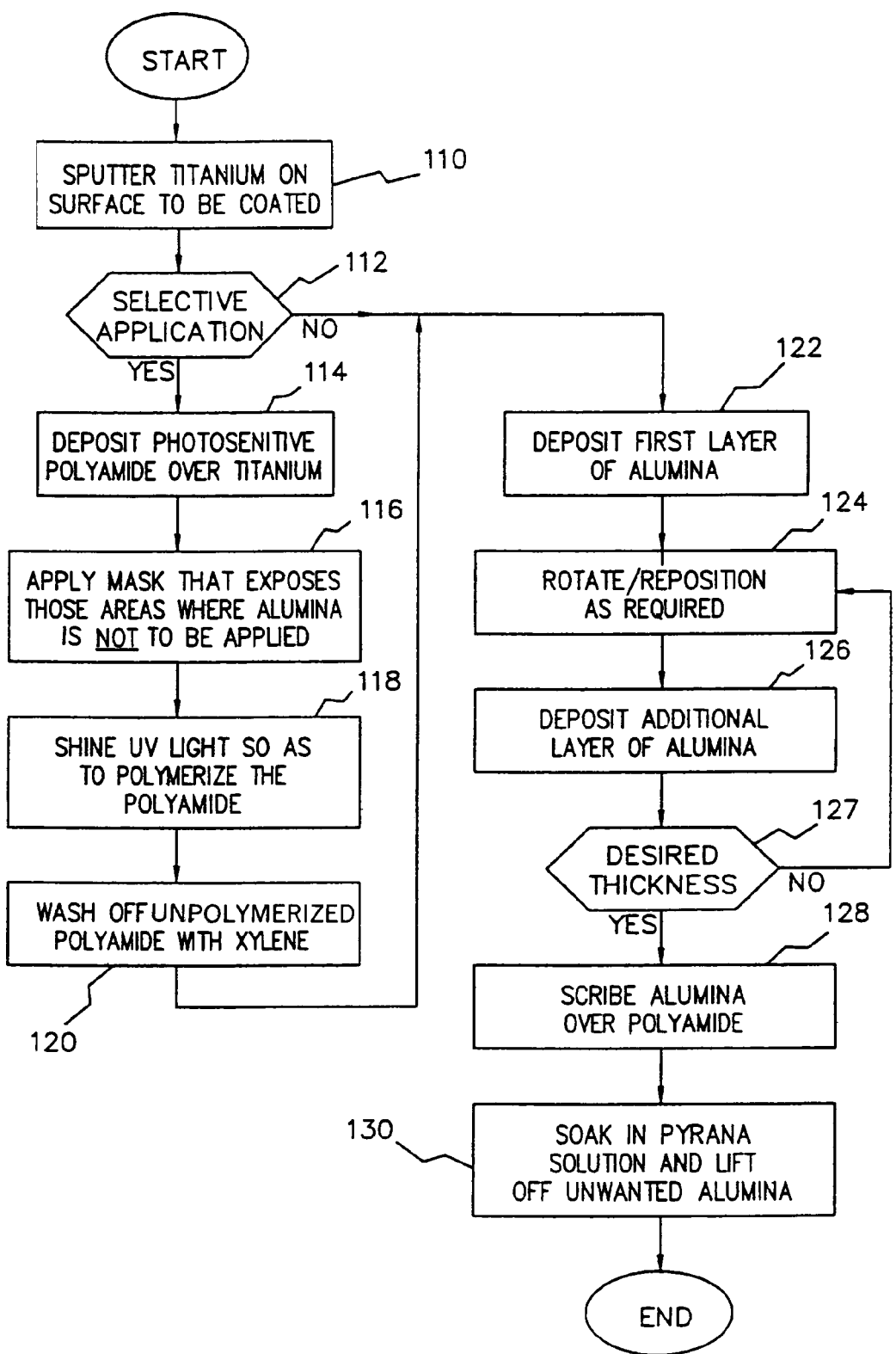
FIG. 5 is a more detailed flow chart of a preferred method of applying a coating to an object in accordance with the invention.

The steps typically followed in applying a coating of-alumina to an object are illustrated in the flow chart of FIG. 5. As seen in FIG. 5, these steps include:

(a) Sputtering a layer of titanium of about 300 Å thick over any metal conductor or other object that is to be coated with the alumina (block 110 of FIG. 4).

(b) If selective application of the alumina to the object is to be made (YES branch of block 112), spinning a photo-sensitive polyamide onto a ceramic hybrid substrate, or other component to be encapsulated with the alumina or other substance (block 114).

(c) Applying a mask that exposes those areas where Alumina is not to be applied (block 116).

(d) Shining ultra violet (UV) light through the mask to polymerize the polyamide (block 118). Where the UV light illuminates the polyamide is where aluminum oxide will not be deposited. Thus, the polymerization of the polyamide is, in effect, a negatively acting resist.

(e) Developing the photoresist by washing off the unpolymerized polyamide with xylene (block 120), or an equivalent substance. Once the unpolymerized polyamide has been washed off, the ceramic (or other component) is ready for aluminum oxide deposition.

(f) If selective application of the alumina is not to be made (NO branch of block 112), i.e., if alumina is to be applied everywhere, or after washing off the unpolymerized polyamide (block 120), depositing aluminum oxide to a prescribed thickness, e.g., between 4 and 10 microns, e.g., 6 microns, over the object using ion enhanced evaporation (or sputtering), IBD, or other suitable application techniques (block 122).

(g) During application of the coating, rotate and/or reposition the object as required (block 124) in order to coat all sides of the object, e.g., as shown in FIG. 4, with a coating of sufficient thickness. This step may require several iterations, e.g., incrementally depositing a thin layer of alumina (block 126), checking the layer, for the desired thickness or properties (block 127), and repeating the repositioning (block 124), depositing (block 126), and checking (block 127) steps as required until a desired thickness is achieved, or until the coating exhibits desired insulative and/or hermeticity properties.

(h) Breaking or scribing the aluminum oxide that resides over the polyamide, if present, with a diamond scribe, or laser, controlled by a computerized milling machine (block 128). This permits a pyrana solution, explained below, to set under the oxide for subsequent lift off of the aluminum oxide.

(i) Lifting off the polyamide and unwanted aluminum oxide after soaking the substrate in pyrana solution ($H_2SO_4 \times 4 + H_2O_2 \times 2$ heated to 60° C.) (block 130). Soaking should occur for 30 to 60 minutes, depending on the thickness of the polyamide layer.

For some applications, the device to be coated may comprise an entire IC chip or a permanent magnet, e.g., a small ceramic magnet. When an IC chip or a magnet is to be coated with alumina, a similar process to that described above is followed, except that there are no metal traces or pads that need to be deposited or covered. Rather, the entire chip or magnet is coated with one or more layers of alumina.

Leakage tests and voltage breakdown tests, when applicable, may also be performed in conventional manner in order to determine the insulative and/or sealing properties of the coating. Typically, the device or component is immersed in a saline solution representative of living body tissue. Next, a voltage is applied between a metal trace covered by the alumina and a platinum black electrode, or other reference electrode, positioned proximate the covered device. The voltage is slowly increased while watching/monitoring the current drain. The voltage increase is stopped and measured at the point where breakdown occurs. Leakage current is measured by keeping the applied voltage at a constant value and monitoring the current drain.

Figure 6:
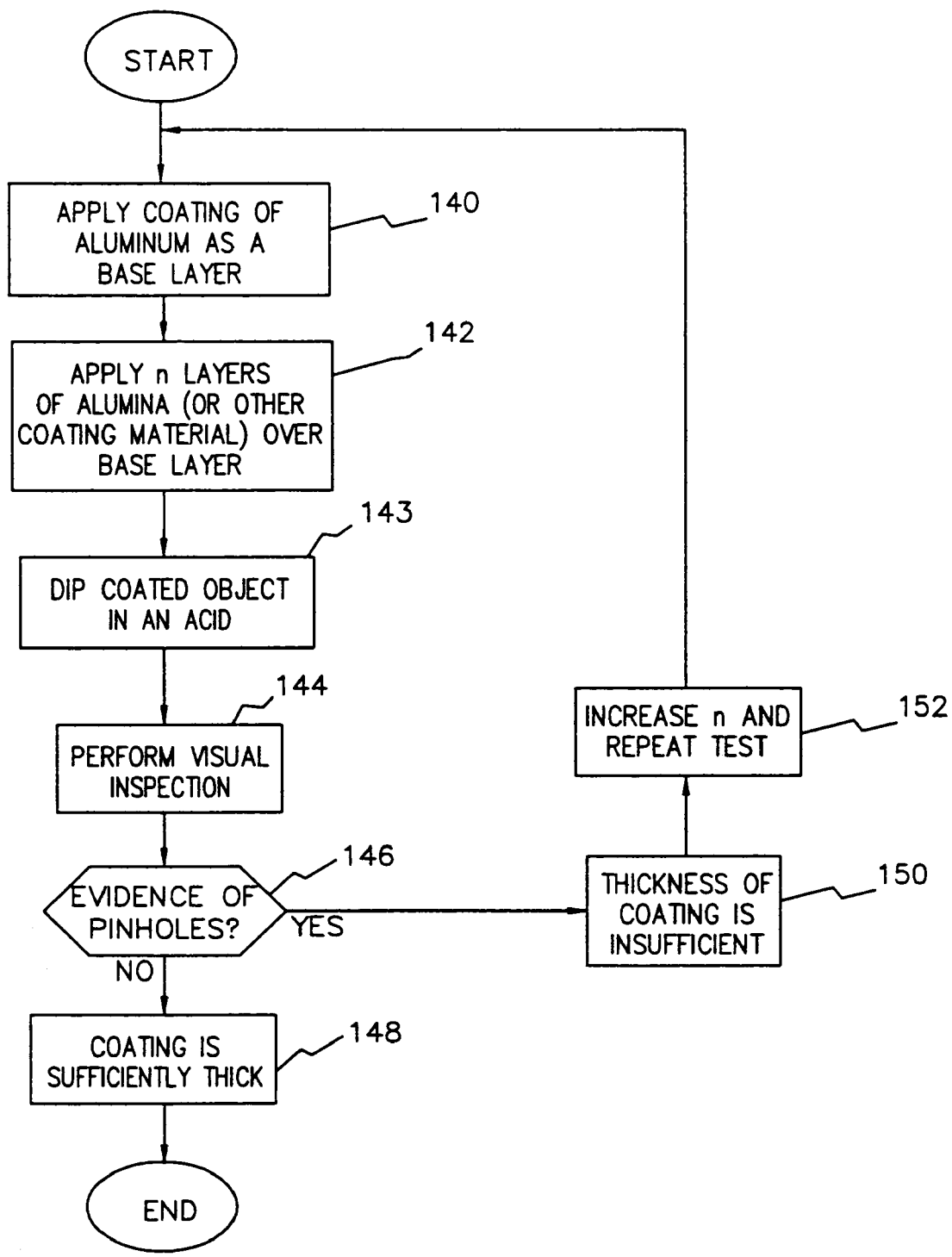
FIG. 6 is a flow chart that illustrates a preferred test used to determine how many layers of a coating need to be applied, i.e., how thick of a coating is needed, in order to provide a coating free of micro-holes (also called "pin-holes").

A useful test for determining how thick the alumina coating must be to eliminate micro-holes, or pinholes, is shown in the flow diagram of FIG. 6. As seen in FIG. 6, a first step is to apply a layer of pure aluminum to a test object (block 140). This layer of pure aluminum serves as a base layer. Then, n layers of a suitable oxide, such as alumina, are applied over the base layer, where n is an integer of from e.g., 1 to 5. Each of these n oxide layers are applied in a controlled manner, using, e.g., IBD techniques, so that each deposited layer has a thickness that is more or less consistent, e.g., 1-2 microns. After application of n layers of alumina (or other ceramic), the coated device is dipped in an acid (block 143). If any pinholes are present in the coating, then the acid immediately starts to react with the aluminum base layer, leaving a very detectable ring. Thus, by performing a simple visual inspection of the device (block 144), one can easily determine whether there is any evidence of pinholes (block 146). If evidence of pinholes is seen (YES branch of block 146), then that is evidence that the n layers of alumina that were deposited did not create a sufficiently thick coating (block 150). Thus, the value of n is increased (block 152), and the test is repeated. If no evidence of pinholes is seen (NO branch of block 146), then that is evidence that the alumina coating is sufficiently thick.

Generally, 4-6 layers of alumina, creating a total coating thickness of 5-10 microns, is sufficient to reduce leakage current to less than about 6 pa. For desired hermeticity, at least about 6 layers of alumina are typically required.

It is to be emphasized that while using alumina in an implanted device is not new, depositing extremely thin layers of alumina, e.g., 5 to 10 microns thick, over components or devices to be implanted, and then relying on such thin layer of alumina to act as an insulative layer or coating, is new, and has produced surprising and unexpected results relative to its insulative properties.

EXAMPLE

A test specimen that included a plurality of 75 mil by 25 mil and 75 mil by 5 mil metallized pads deposited on an alumina substrate was constructed using conventional techniques. The plurality of metallized pads are separated from one another by a distance of about 2.0-2.5 mils. A layer of alumina insulator approximately 5-6 microns thick was deposited on and between the metallized pads using an ion-enhanced evaporative sputtering technique. The ion-enhanced evaporative sputtering was performed in an evacuated chamber at a moderate temperature of about 60-100° C., and allowed to cure for approximately 0.5-4 hours. The test specimen was subsequently submersed in a saline solution at 87° C. for three months. Leakage current between the metallized pads and the saline solution was measured and did not exceed 10 pA across the 6 micron size insulating layer. In addition leakage current between each metallized pads did not exceed 10 pA across the 2.0-2.5 mil spacings.

What is claimed is:

1. A method of forming insulated conductive patterns on a substrate, the method comprising:
   forming conductive patterns on a surface of the substrate;
   forming a layer of titanium on the conductive patterns; and
   forming a layer of ceramic material over the surface of the substrate including the conductive patterns that is about 5-10 microns thick.

2. The method recited in claim 1, wherein the conductive patterns are metallized traces.

3. The method recited in claim 2, wherein the metallized traces are formed by thin film deposition.

4. The method recited in claim 2, wherein the metallized traces are formed by thin film deposition and etching.

5. The method recited in claim 1, wherein the layer of titanium is about 300 angstroms thick.

6. The method recited in claim 1, wherein the ceramic material is selected from the group consisting essentially of alumina, zirconia, magnesium oxide, alloy of alumina, alloy of zirconia, and alloy of magnesium oxide.

7. The method recited in claim 1, wherein the layer of ceramic material is formed in successive layers.

8. The method recited in claim 7, wherein each of the successive layers is about 1-2 microns thick.

9. The method recited in claim 1, wherein the layer of ceramic material is formed using an ion-enhanced deposition technique.

10. The method recited in claim 1, wherein the layer of ceramic material is formed using an ion-beam deposition (IBD) technique.

* * * * *